United States Patent [19]

Pilgrimm

[11] Patent Number: 5,928,958
[45] Date of Patent: Jul. 27, 1999

[54] SUPERPARAMAGNETIC PARTICLES, PROCESS FOR THEIR MANUFACTURE AND USAGE

[76] Inventor: Herbert Pilgrimm, Sophie-Charlotte-STR.27a, D-14169 Berlin, Germany

[21] Appl. No.: 08/776,131

[22] PCT Filed: Jul. 27, 1995

[86] PCT No.: PCT/DE95/01028

§ 371 Date: Jan. 8, 1997

§ 102(e) Date: Jan. 8, 1997

[87] PCT Pub. No.: WO96/03653

PCT Pub. Date: Feb. 8, 1996

[30] Foreign Application Priority Data

Jul. 27, 1994 [DE] Germany .............................. 44 278 21

[51] Int. Cl.$^6$ .......................... G01N 33/553; A61K 9/16; C07K 17/14
[52] U.S. Cl. ..................... 436/526; 424/9.323; 424/9.34; 424/9.35; 530/391.1
[58] Field of Search ......................... 436/526; 424/9.323, 424/9.34, 9.35; 530/391.1

[56] References Cited

FOREIGN PATENT DOCUMENTS

| | | |
|---|---|---|
| 156537 | 10/1985 | European Pat. Off. . |
| 176638 | 4/1986 | European Pat. Off. . |
| 184710 | 6/1986 | European Pat. Off. . |
| 284549 | 3/1988 | European Pat. Off. . |
| 321322 | 6/1989 | European Pat. Off. . |
| 332022 | 9/1989 | European Pat. Off. . |
| 4309333 | 9/1994 | Germany . |
| WO 9326019 | 12/1993 | WIPO . |
| WO 9409368 | 4/1994 | WIPO . |
| WO 9411103 | 5/1994 | WIPO . |

OTHER PUBLICATIONS

WPI Abstract of Japanese patent JP 1,315,494, Dec. 1989.

*Primary Examiner*—Mary E. Ceperley
*Attorney, Agent, or Firm*—Collard & Roe, P.C.

[57] ABSTRACT

Superparamagnetic particles consist of superparamagnetic one-domain particles and aggregates of superparamagnetic one-domain particles to whose surfaces are bound organic substances optionally having further binding sites for coupling to tissue-specific binding substances, diagnostic or pharmacologically active substances. The superparamagnetic particles consist of a mixture of small superparamagnetic one-domain particles with a particle size from 3 to 50 nanometers and stable, degradable aggregates of small superparamagnetic one-domain particles with a particle size from 10 to 1000 nanometers. They are made of iron hydroxide, iron oxide hydrate, iron oxides, iron mixed oxides or iron to the surface of which are bound mono- and/or polyhydroxylic group-containing aromatic substances, polyglycerines, amino-acid-containing substances, silicate group-containing substances among the orthosilicic acids and their condensation products and phosphate group-containing substances among the ortho- or metaphosphoriic acids and their condensation products. These substances may have further binding sites. These new particles may be used to destroy tumors, increase immunity, in magnetic drug targeting, for cell fusion, gene transfers, as contrasting agents, for in vitro diagnosis, as magnetic ion exchangers and magnetic adsorbents, if required by exposure to magnetic fields.

5 Claims, No Drawings

SUPERPARAMAGNETIC PARTICLES, PROCESS FOR THEIR MANUFACTURE AND USAGE

The present invention relates to superparamagnetic particles consisting of superparamagnetic one-domain particles and aggregates of superparamagnetic one-domain particles of iron oxides, mixed iron oxides or iron to whose surfaces are bound organic substances which optionally may have further binding sites for coupling tissue-specific binding substances, diagnostic substances or pharmacologically active substances.

Patent EP-B-0284549 describes superparamagnetic one-domain particles of iron oxide, mixed iron oxide or iron with a particle size ranging from 3 to 20 nanometers, to whose surfaces are chemically bound organic substances of the group of phosphate, diphosphate, polyphosphate, thiophosphate, phosphonate or thiophosphonate group-containing polyalkylene glycols, phosphate group-containing nucleotides, their oligomers or their polymers as well as phosphate group-containing carbohydrates, which may have further binding sites.

Patent DE-A-4309333 describes stable, degradable aggregates with a particle size ranging from between 10 and 1000 nanometers with defined behaviour in a magnetic field whereby the aggregates consist of several small superparamagnetic one-domain particles of iron oxide, mixed iron oxide or iron with a particle size ranging from 3 to 20 nanometers to whose surfaces are chemically bound substances of the group of phosphate, diphosphate, polyphosphate, thiophosphate, phosphonate or thiophosphonate group-containing polyalkylene glycols, carbohydrates or of the phosphate group-containing nucleotides, their oligomers or their polymers.

The object of the invention is to enlarge the range of substances which can be bound to the surfaces of the one-domain particles, in order to optimally adapt the physicochemical and physiological properties of the magnetic particles being formed to the respective fields of application whereby these substances should be stable and easy to manufacture.

A surprising finding was that mono- and polyhydroxylic group-containing aromatic substances, polyglycerin and their phosphate, diphosphate, polyphosphate, thiophosphate, phosphonate, thiophosphonate, carboxylate, sulphate, mercapto or silantriol group-containing derivatives, amino acid containing oligopeptides, polypeptides, proteins, proteids as well as their derivatives and denaturation products, mercapto and amino group-containing substances such as biotin, mercaptopurine, -cytosin, -guanine, -uracil, -thymine, -hypoxanthine, as well as their mercaptonucleosides and mercapto-desoxynucleosides, ortho-silicic acid and their condensation products with bivalent and polyvalent inorganic ions and/or organic acids and bases and ortho- or metaphosphoric acid and their condensation products enter stable bindings with the surface of the superparamagnetic particles leading to stable magnetic liquids and aggregation-stable, superparamagnetic aggregates.

According to the invention, stabilisation of the magnetic particles takes place by binding mono- and polyhydroxylic group-containing aromatic substances such as for example benzenoids, coumarins, lignans, terphenyls, flavonoids, tannins, xanthenes, benzophenones, naphthalenes, naphthoquinones, anthraquinones, anthracyclines, polycyclic condensated aromatic compounds and their phosphate, diphosphate, polyphosphate, thiophosphate, phosphonate, thiophosphonate, carboxylate, sulphate, mercapto or silantriol group-containing derivatives, of polyhydroxylic group-containing substances, selected from among polyglycerins and their phosphate, diphosphate, polyphosphate, thiophosphate, phosphonate, thiophosphonate, carboxylate, sulphate, mercapto or silantriol group-containing derivatives, of amino acid containing substances such as for example oligopeptides, polypeptides, proteins, proteids as well as their derivatives and denaturation products, of mercapto- and amino group-containing substances such as for example biotin, mercaptopurine, -cytosin, -guanine, -uracil, -thymine, -hypoxanthine, as well as their mercaptonucleosides and mercapto-desoxynucleosides, of silicate group-containing substances of ortho-silicic acid and their condensation products with bivalent and polyvalent inorganic ions an/or organic acids and bases, of phosphate group containing substances of ortho- or metaphosphoric acid and their condensation products, on the surface of the magnetic particles.

Apart from these stabiliser substances, it is possible to bind additional organic substances to the surface of the magnetic particles in order to better adjust the properties of the magnetic particles to the desired requirements. This includes organic substances of the group of phosphate, diphosphate, carboxylate, polyphosphate, thiophosphate, phosphonate, thiophosphonate, sulphate, sulphonate, mercapto, carboxylate, silantriol group-containing polyalkylene glycols, and carbohydrates, of the phosphate group-containing nucleotides, their oligomers or their polymers, of the alkyl, aryl and/or alkyl-aryl-polyethylene glycol phosphates or phosphonates, of the group of nitrogenous polysaccharides, selected from among mucopolysaccharides, glycoproteids, chitins, as well as their derivatives and denaturation products.

The following are examples of stabiliser substances for mono- and/or polyhydroxyl group-containing aromatic substances: caffeic acid, gallic acid, hexahydroxydiphenic acid, ellagic acid, chebulic acid, and their derivatives and denaturation products with carbohydrates and phenol carbonic acids, aesculin, rutin, aescin, troxerutin, hesperidin, aloin, kaempferol, quercetin, gallotannin, ellagitannin, ruberythrinic acid, carminic acid, natural and synthetic dyes such as anthraquinone or phthalocyanin dyes, daunorubicin, ansamycin as well as their phosphate, diphosphate, polyphosphate, thiophosphate, phosphonate, thiophosphonate, carboxylate, sulphate, mercapto or silantriol group-containing derivatives.

The following are examples of stabiliser substances for substances containing amino acid of the groups of oligopeptides, polypeptides, proteins, proteids as well as their denaturation products: protamines, glutelins, albumins, globulins, gelatine, casein-hydrolysates.

Examples of stabiliser substances for substances containing mercapto and amino groups are: biotin, cysteine, methionine, glutathione, mercaptopurine, -cytosin, -guanine, -uracil, -thymine, -hypoxanthine, as well as their mercaptonucleosides and mercapto-desoxynucleosides.

By way of example, stabiliser substances for silicate group-containing condensation products of ortho-silicic acid with bi- and polyvalent inorganic ions are the condensation products with the elements Al, Au, Bi, Cr, J, Mo, P, Pt, Se, Tc, Ti, Y, Zr and rare precious metals.

By way of example, stabiliser substances for silicate group-containing condensation products of ortho-silicic acid with organic acids and bases are their condensation products with phytic acid, alginic acid, gallic acid.

By way of example, stabiliser substances for phosphate group-containing condensation products of ortho- or metaphosphoric acid are pyrophosphoric acid, polyphosphoric acids, cyclophospates and hetero condensation products and water insoluble salt compounds with inorganic ions, such as Ag, Au, Bi, Mo, Pt, Tc, Y, Zr, and basic group-containing organic compounds such as spermine, spermidine, polyethylene imine, oxygelatine.

The stabiliser substances may be manufactured according to the current state of technology, or purchased.

According to the invention, to the stabilisation molecules—to whose surfaces are bound hydroxyl group-containing aromatic substances, polyhydroxyl group-containing polyglycerins, amino acid containing substances, silicate group-containing substances and phosphate group-containing substances at the surface of the super paramagnetic particles—the following can be bound: tissue-specific binding substances such as for example antigens, antibodies, ribonucleic acids, desoxyribonucleic acids, ribonucleic acid sequences, desoxyribonucleic acid sequences, haptens, avidin, streptavidin, protein A, protein G, endotoxin-binding proteins, lectin, selectin, pharmacologically active substances such as for example anti tumour proteins, enzymes, anti tumour enzymes, antibiotics, plant alkaloids, alkylation reagents, antimetabolites, hormones and hormone antagonists, interleukins, interferons, growth factors, tumour necrosis factors, endotoxins, lymphotoxins, urokinase, streptokinase, plasminogen-streptokinase activator complex, tissue plasminogen activators, desmodus plasminogen activators, macrophage activating bodies, antisera, protease inhibitors, substances containing radioactive isotopes, tensides, cardiovascular pharmaceutic products, chemotherapeutic products, gastrointestinal pharmaceutic products, neuropharmaceutic products, pharmacologically active cells such as for example organelles, viruses, microbes, algae, fungi, in particular erythrocytes, thrombocytes, granulocytes, monocytes, lymphocytes, Langerhans islands, pharmacologically active complexing agents, such as for example polycarbonic acids, polyaminocarboxylic acids, porphyrins, catecholamines, cell-fusioning substances such as for example polyethylene glycols, alkyl polyethylene glycols, alkyl aryl polyethylene glycols, water-miscible polypropylene glycols $(PPG)_m$ or water-miscible substance copolymerides of polyethylene glycol (PEG) and polypropylene glycol (PPG), selected from among the substance copolymerides $(PEG)_n$-$(PEG)_m$, $(PEG)_n$-$(PPG)_m$-$(PEG)_n$, $(PPG)_m$-$(PEG)_n$-$(PPG)_m$ whereby n and m are positive whole numbers, selected for PEG in the range of 4 to 1000, for PPG in the range of 3 to 12 and for PEG-PPG substance copolymerides in the range 3 to 140, and/or substances acting as gene-transfer media, such as for example polyethylene glycols and their derivatives and polyalkylene imines, such as for example pentaethylene hexamine, polyethylene imine, spermine, spermidine.

The superparamagnetic particles according to the invention, which were stabilised with hydroxylic group-containing aromatic stabiliser substances, adsorb compounds with a relatively high content of amino acid and aromatic compounds, so that in some applications a purely adsorptive binding of tissue-specific binding substances, pharmacologically active substances and pharmacologically active cells is sufficient to be able to apply them for magnetic drug targeting or as a contrast medium.

The superparamagnetic particles according to the invention, which were stabilised with polyglycerins and their derivatives, can be used for many coupling reactions during which the reactivity of the phosphate, diphosphate polyphosphate, thiophosphate, phosphonate, thiophosphonate, carboxylate, sulphate, mercapto or silantriol group-containing derivatives is applicable for binding tissue-specific binding substances, pharmacologically active substances, pharmacologically active cells, pharmacologically active complexing agents, cell-fusioning substance and/or substance acting as gene-transfer medium.

The superparamagnetic particles according to the invention, which were stabilised with amino acid group-containing stabiliser substances can be used for many coupling reactions during which the reactivity of the amino acid groups is applicable for chemical binding of tissue-specific binding substances, pharmacologically active substances, pharmacologically active cells, pharmacologically active complexing agents, cell-fusioning substance and/or substance acting as gene-transfer medium.

The superparamagnetic particles according to the invention, which were stabilised with silicate group-containing substances of ortho-silicic acid and their condensation products with organic acids and bases, can be used for adsorptive bindings and for many coupling reactions during which the reactivity of the functional groups of the organic acids and basis which have formed stable condensation products with the silicate groups, for chemical binding of tissue-specific binding substances, pharmacologically active substances, pharmacologically active cells, pharmacologically active complexing agents, cell-fusioning substance and/or substance acting as gene-transfer medium is applicable.

Coupling to the superparamagnetic particles of tissue-specific binding substances, pharmacologically active substances, pharmacologically active cells, pharmacologically active complexing agents, cell-fusioning substances or substances acting as gene-transfer medium furthermore has the advantage that by way of relaxation-time changes of the resonance-capable hydrogen atoms in the body, the therapy progress can be observed by means of nuclear spin diagnostics.

Manufacture of superparamagnetic particles is by precipitation from a solution of ferric salt with an alkaline lye or aqueous ammonia and a subsequent targeted agglomeration of the resulting superparamagnetic one-domain particles. Thereby, the superparamagnetic one-domain particles are stirred in water and, at a pH value of 1 to 7, brought to aggregation, by heating to 80 to 120° C.—in the case of temperatures exceeding 100° C. in an autoclave.

After cooling the dispersion, the particles are washed until such time as the electrical conductivity of the filtrate is <10 $\mu$S/cm. The superparamagnetic particles thus manufactured immediately form a rapidly sedimenting precipitation which even through vigorous stirring or ultra sound treatment cannot be transformed into a stable dispersion. Only binding of stabiliser substances at the surface of the superparamagnetic particles provides dispersability.

In the case of some stabiliser substances it is sufficient to stir with a glass rod, other stabiliser substances need higher energy input, such as for example heating or the effect of ultrasound, in order to obtain stable dispersions.

Depending on the field of application, the magnetic dispersions can be dialyzed in order to remove the excess stabiliser substance.

The stabilised superparamagnetic particle dispersions contain the superparamagnetic one-domain particles which are not yet aggregated or only weakly aggregated. These form a stable magnetic liquid which is easily separated from the larger superparamagnetic particles by their sedimentation in a magnetic field of corresponding strength and inhomogeneity. The stabilised superparamagnetic one-domain particles are easily used as a contrast medium for nuclear spin diagnostics, as cell fusioning substances or as gene-transfer medium whereby here too, the efficacy of cell fusion and gene transfer can be examined by way of nuclear spin diagnostics.

In a simple embodiment of magnetic separation, a glass beaker of the magnetic dispersion is placed on a permanent magnet with a magnetic flux density of 0.1 T and after a sedimentation period of approx. 30 min, the magnetic liquid above the sediment is poured away. The superparamagnetic aggregates remain. Depending on particle size they spontaneously disperse again in the dispersion or remain as sediment in the glass beaker. Up to a particle size of approx. 500 nm the superparamagnetic particles disperse again spontaneously or through gentle stirring in the aqueous dispersion medium.

Sedimentation stability of the superparamagnetic aggregates according to the invention is significantly higher than in the magnetic particles, known so far, with comparable magnetic properties. This can probably be attributed to the pronounced structuring of the water molecules surrounding the superparamagnetic particles and the resulting increased Stokes' particle diameter.

Since the proportion of superparamagnetic one-domain particles in the superparamagnetic aggregates is significantly higher than in the magnetic particles known so far, the precipitation rate of the superparamagnetic aggregates in an inhomogenous magnetic field is also higher. In a 10% by weight aqueous dispersion of superparamagnetic particles, with a diameter of approx 100 nm and a magnetite content of 95%, the precipitation time of the magnetic particles on a permanent magnet with a magnetic flux density of 0.1 T is less than 1 min.

As aggregates, the superparamagnetic particles according to the invention have an iron oxide content of 90 to 98% by weight. When compared to the state of technology whereby magnetic particles can contain up to 60% by weight iron oxide, this means a significant improvement in the magnetic properties. Thus, to achieve the same magnetic interaction, the new superparamagnetic particles can be accordingly smaller than the magnetic particles known up to now. The specific surface enlarges; more pharmacologically active substances or tissue-specific binding substances can be coupled to the surface. A decrease in particle size also improves biological compatibility which increases the rate of degradability in the body. Also the free available time of the magnetic particles during magnetic drug targeting, i.e. the time until the particles are bound by the reticulo endothelial system, increases with a decrease in particle size.

Depending on particle size and composition of the stabiliser substances, bio-availability of the superparamagnetic particles in the body ranges only from a few minutes to several hours, i.e. the superparamagnetic particles are bound relatively quickly by the reticulo endothelial system.

By means of examples, the manufacture of superparamagnetic particles according to the invention is described.

EXAMPLE 1

Dissolve iron (III) chloride (270 g) and iron (II) sulphate (153 g) in 1 l distilled water. Set a pH value of 9.5 by adding caustic soda while stirring. After completed precipitation set the pH value to 5.0 by stirring and adding hydrochloric acid and heat to 100° C. After cooling the dispersion, wash the precipitation, until the electrical conductivity of the filtrate is <10 $\mu$S/cm. Stabilising of the superparamagnetic particles takes place by mixing an aqueous stabiliser solution or a stabiliser solution containing low-boiling polar solvents with the magnetic particles at room temperature. In this, the stabiliser solution, depending on the desired properties, can consist of pure stabiliser substances or of mixtures of stabiliser substances. In order to accelerate dispersion and stabilisation, the dispersion can be stirred or treated with ultrasound. If low-boiling organic solvents are used, these will be removed after stabilisation, by vacuum evaporation or dialysis.

EXAMPLE 2

Dissolve iron (III) chloride (270 g) and iron (II) chloride (119 g) in 1 l distilled water. Set a pH value of 9.6 by adding ammoniacal gas liquor while stirring. After completed precipitation set the pH value to 6.0 with hydrochloric acid, add 20 ml hydrogen peroxide (30%), and heat to 100° C. After cooling, wash the precipitation with distilled water until the electrical conductivity of the filtrate is <10 $\mu$S/cm. The resulting g-$Fe_2O_3$ can be stabilised.

EXAMPLE 3

Dissolve iron (III) chloride (270 g) and iron (II) sulphate (153 g) in 1 l distilled water. By adding caustic soda while stirring set a pH value of 9.5. After completed precipitation add 20 g polyphosphoric acid to the dispersion while stirring and heat to 100° C. After cooling the dispersion, wash the precipitation, until the electrical conductivity of the filtrate is <10 $\mu$S/cm. Stir the solid matter into 300 ml of water and disperse with ultrasound for 20 min at 100 W. Sediment the resulting dispersion for 30 min on a permanent magnet with a magnetic flux density of 0.1 T and pour away the magnetic liquid above the sediment. The liquid above the sediment predominantly contains stabilised superparamagnetic one-domain particles. The sediment on the permanent magnet contains the superparamagnetic degradable aggregates. By means of repeated washing with distilled water and renewed sedimentation in the magnetic field, the superparamagnetic aggregates can be obtained pure and with close particle size distribution. The average particle diameter of superparamagnetic particles is approx. 80 nm.

EXAMPLE 4

Stir the entire quantity of liquid above the sediment, of the superparamagnetic one-domain particles stabilised with polyphosphoric acid from example 3 into a solution of 20 g oxypolygelatine in 400 ml physiological table salt solution. The resulting magnetic liquid can be used as an i.v. contrast medium for nuclear spin diagnostics.

EXAMPLE 5

Stir the entire quantity of the magnetite sediment stabilised with polyphosphoric acid from example 3 into 300 ml water, set to a pH of 1.0 with hydrochloric acid (10%), add a mixture of 28.4 g bismuth chloride in 20 ml concentrated hydrochloric acid and subsequently set the pH to 2.5 by means of caustic soda. Into this dispersion stir a solution of 30 g sodium silicate in 200 ml distilled water and disperse for 10 min with ultrasound at 100 W. Separation of the non-agglomerated or only weakly agglomerated superparamagnetic one-domain particles which form a stable magnetic liquid is by magnetic sedimentation as described in example 3. The superparamagnetic one-domain particles and the superparamagnetic aggregates are highly suitable as oral contrast medium for nuclear spin diagnostics and x-ray diagnostics.

EXAMPLE 6

For stabilisation, stir the entire quantity of the magnetite sediment from example 1 into a solution of 30 g gallic acid into 400 ml distilled water and disperse with ultrasound for 10 min at 100 W. Separation of the non-agglomerated or only weakly agglomerated superparamagnetic one-domain particles which form a stable magnetic liquid is by magnetic sedimentation as described in example 3. The superparamagnetic aggregates are highly suitable for magnetic enrichment in tumours. Here, by means of magnetomechanical immune stimulation, or additionally by hyperthermia, i.e. by irradiation of electromagnetic radiation and warming the tumour, they can destroy the tumour. The superparamagnetic one-domain particles can be employed as an oral or i.v. contrast medium for nuclear spin diagnostics.

EXAMPLE 7

Place the entire quantity of the magnetite sediment from example 1 into a solution of 40 g methoxy polyethylene glycol phosphate (MG 2000) and 20 g rutinoside in 300 ml methanol and disperse with ultrasound for 5 min at 100 W. Subsequently, add 500 ml distilled water to the dispersion and distil the methanol off. Disperse the aqueous solution once more with ultrasound for 20 min at 100 W. Separation of the non-agglomerated or only weakly agglomerated superparamagnetic one-domain particles which form a stable magnetic liquid is by magnetic sedimentation as described in example 3. The superparamagnetic aggregates can be employed for parenteral tumour damage because, as shown in tests with laboratory mice and rats, a strong activation of the immune system takes place which can lead to total remission of tumours. In addition, the superparamagnetic aggregates are suitable for coupling to tissue-specific binding substances, pharmacologically active substances and pharmacologically active cells. The superparamagnetic one-domain particles can be employed as parenteral contrast medium for nuclear spin diagnostics to depict the vascular system and the gastro-intestinal tract or as a vector for gene transfer.

EXAMPLE 8

20 ml of the dispersion of the superparamagnetic aggregates from example 7, with a magnetic saturation induction of 10 mT, are mixed with a solution of 10 mg doxorubicin in a solution of 10 ml physiological table salt. These superparamagnetic particles are very well suited for magnetic enrichment in tumours. The strong activation of the immune system by the superparamagnetic particles can lead to tumour damage which can be enhanced by the effect of the cytostatic substance.

EXAMPLE 9

Add the entire quantity of the g-$Fe_2O_3$ sediment from example 2 to a solution of 30 g tannic acid in 500 ml water and stir for 5 min and disperse for 10 min in an ultrasound dispergator (at 100 W). Dialyse the resulting dispersion with a 50 kD filter against distilled water, in order to remove excessive stabiliser substance. Separation of the non-agglomerated or only weakly agglomerated superparamagnetic one-domain particles which form a stable magnetic liquid is by magnetic sedimentation as described in example 3. The resulting superparamagnetic aggregates, whose average particle diameter is approx. 80 nm, are suitable for coupling to tissue-specific binding substances containing amino acid, to pharmacologically active substances and pharmacologically active cells. The superparamagnetic one-domain particles can be employed as an oral or i.v. contrast medium for nuclear spin diagnostics.

EXAMPLE 10

20 ml of the superparamagnetic aggregates from example 9, with a magnetic saturation induction of 10 mT, are mixed with a solution of 10 mg mitoxantrone in 20 ml of an acetate-buffered physiological table salt solution.

These superparamagnetic particles are highly suitable for magnetic enrichment in tumours. Here they can lead to tumour damage by magnetic enrichment in the tumour and enhanced desorption of the cytostatic substance under the effect of the non-homogenous magnetic field.

EXAMPLE 11

Place the entire quantity of the magnetite sediment from example 1 into a solution of 20 g oxypolygelatine in 400 ml distilled water, stir for 5 min and wash until the electrical conductivity of the filtrate is <100 $\mu$S/cm. Disperse the suspension with ultrasound for 10 min at 100 W. Separation of the non-agglomerated or only weakly agglomerated superparamagnetic one-domain particles which form a stable magnetic liquid is by magnetic sedimentation as described in example 2. The superparamagnetic one-domain particles can be employed as parenteral contrast medium for nuclear spin diagnostics to depict the vascular system.

EXAMPLE 12

Add the entire quantity of the magnetite sediment from example 2 to a solution of 40 ml of a solution of 40% phytic acid in 500 ml distilled water, stir for 5 min and disperse for 10 min in an ultrasound dispergator (100 W) Titrate the resulting dispersion with a 30% solution of sodium silicate to a pH value of 7.0, disperse for 10 min in an ultrasound dispergator (100 W) and sediment for 30 min on a permanent magnet with a magnetic flux density of 0.1 T and suck off the magnetic liquid above the sediment. The sediment on the magnetic field contains the superparamagnetic particles. By means of repeated washing with distilled water and renewed sedimentation in the magnetic field, the superparamagnetic particles can be obtained pure and with close particle size distribution. The superparamagnetic particles, having an average particle diameter of approx. 160 nm, are suitable for the coupling of tissue-specific binding substances containing amino acid, of pharmacologically active substances and pharmacologically active cells.

The main application of the superparamagnetic particles according to the invention is in the areas of magnetic drug targeting, contrast mediums, cell fusion and gene transfer.

Because of the very high proportion of magnetic material (90 to 98% by weight) even small magnetic particles can be concentrated very well and very quickly in certain regions of the body, by means of electromagnetic or permanent-magnetic fields. The superparamagnetic aggregates according to the invention can be employed for parenteral tumour damage, because injection of these aggregates into the bloodstream causes strong activation of the immune system which can lead to total remission of tumours. By coupling pharmacologically active substances to the superparamagnetic aggregates, their concentration at the place of action can be increased, in particular when using tumour-specific antibodies. This circumstance is significant for cancer therapy, because the substances used in chemotherapy of tumours have very severe side-effects on the entire organism and because with enrichment at the point of action the remaining body is not burdened as much with cytostatic substances or radioactive isotopes.

When coupling nucleides, nucleic acids, antimetabolites or antitumoral or antiviral derivatives to the superparamagnetic aggregates, their concentration at the place of action can be drastically increased, in particular when employing them in gene therapy. By coupling them to viruses, bacteria, cells and their surface molecules, the superparamagnetic particles can be employed for immune-activation in the body, whereby the effect of magnetic fields supports immune activation.

In magnetic drug targeting, the quantity of superparamagnetic particles to be used is dependent on the particle size, the composition of the stabiliser substances, the presence of binding-specific antibodies and the strength of the magnetic field at the place of action. The superparamagnetic particles according to the invention may be used as oral and parenteral contrast medium for nuclear spin diagnostics. When used as parenteral contrast medium the quantity of superparamagnetic particles for the MRI is around 20 mM Fe/kg body weight and when used as an oral contrast medium for the MRI at approx. 10 mM Fe/kg body weight.

In animal experiments, good contrast effects were achieved as a parenteral contrast medium for liver, spleen, bone marrow and blood circulation, for lymphography, as antibody-specific contrast medium for tumour and thrombosis diagnostics and as an oral contrast medium for depicting the gastro-intestinal tract.

The superparamagnetic particles can also be used for in-vitro diagnostics, cell fusion and for gene transfer, optionally with the effect of magnetic fields, if the respective diagnostics, cell-fusioning and gene-transferring substances are bound to the particle surface. Due to the strong magnetic interaction of the superparamagnetic particles with magnetic fields, even very small superparamagnetic particles can easily be separated from the reaction mixture after completion of the diagnostic reaction, cell fusion or gene transfer.

The superparamagnetic particles can also be employed as magnetic ion exchangers and magnetic adsorbents for the separation of ions, organic molecules, macromolecules, cells, viruses etc. in biotechnology, waste-water purification or other mass transfer processes, if the respective ion exchanger groups and adsorbents are bound to the surfaces of the particles.

I claim:

1. Superparamagnetic particles, consisting of particles selected from the group consisting of
   (a) small superparamagnetic one-domain particles of iron hydroxide, iron oxide hydrate, iron oxide, mixed iron oxide or iron with a particle size ranging between 3 and 50 nanometers; and
   (b) dispersion stable, physiological degradable aggregates with a particle size ranging between 10 and 1000 nanometers, whereby the aggregate consists of several small superparamagnetic one-domain particles of iron hydroxide, iron oxide hydrate, iron oxide, mixed iron oxide or iron with a particle size ranging between 3 and 50 nanometers;
   and the mixtures of (a) and (b);
   wherein to the surfaces of the particles or aggregates or mixtures thereof are bound
   (c) substances of the group of
      (i) mono or polyhydroxylic group-containing or both groups containing aromatic substances, selected from among benzenoids, coumarins, lignans, terphenyls, flavonoids, tannins, xanthenes, benzophenones, naphthalenes, naphthoquinones, anthraquinones, anthracyclines, polycyclic condensated aromatic compounds and the phosphate, diphosphate, polyphosphate, thiophosphate, phosphonate, thiophosphonate, carboxylate, sulphate, mercapto or silantriol group-containing derivatives thereof.

2. Superparamagnetic particles according to claim 1, wherein the superparamagnetic one-domain particles (a) and the particles of the stable, degradable aggregates (b) comprise iron hydroxide, iron oxide hydrate, $\gamma$-$Fe_2O_3$, $Fe_3O_4$, mixed iron oxides of the general formula $mMO.nFe_2O_3$, where M represents the bivalent metal ions Fe, Co, Ni, Mn, Be, Mg, Ca, Ba, Sr, Cu, Zn, Pt or mixtures thereof, from the mixed oxides of the general formula $mFe_2O_3.nMe_2O_3$, where Me represents the trivalent metal ions Fe, Al, Cr, Bi, rare earth metals or mixtures of them.

3. Superparamagnetic particles according to claim 1, wherein bound to the superparamagnetic particles are substances selected from the groups
   (i) a tissue-specific binding substance from the group of antigens, antibodies, ribonucleic acids, desoxyribonucleic acids, ribonucleic acid sequences, desoxyribonucleic acid sequences, hapten, avidin, streptavidin, protein A, protein G, endotoxin-binding proteins, lectine, and selectine;
   (ii) a pharmacologically active substance from the group of antitumour proteins, enzymes, antitumour enzymes, antibiotics, plant alkaloids, alkylation reagents, antimetabolites, hormones and hormone antagonists, interleukins, interferons, growth factors, tumour necrosis factors, endotoxins, lymphotoxins, urokinase, streptokinase, plasminogen-streptokinase activator complex, tissue plasminogen activators, desmodus plasminogen activators, macrophagen activating bodies, antisera, protease inhibitors, substances containing radioactive isotopes, tensides, cardiovascular pharmaceutic products, chemotherapeutic products, gastrointestinal pharmaceutic products, and neuropharmaceutic products;
   (iii) pharmacologically active cells from the group of the organelles, viruses, microbes, algae, fungi, in particular erythrocytes, thrombocytes, granulocytes, monocytes, lymphocytes, and Langerhans islands;
   (iv) a pharmacologically active complexing agent from the group of the polycarbonic acids, polyaminocarboxylic acids, porphyrins, and catecholamines;
   (v) cell-fusioning substances from the group of polyalkylene glycols, alkyl polyalkylene glycols, aryl polyalkylene glycols, and alkyl aryl polyalkylene glycols;
   (vi) gene-transfer media from the group of polyalkylene glycols, and poly imines; and
   mixtures of substances of the groups (i)–(vi).

4. Pharmacologically active preparation, consisting of a pharmacologically acceptable carrier and superparamagnetic particles according to claim 1 with the particle size of the one-domain particles between 3 and 50 nm and the aggregates ranging from 10 to 1000 nm, coupled with a tissue-specific binding substance, a pharmacologically active substance, a pharmacologically active cell, a pharmacologically active complexing agent, a cell-fusioning substance or a gene-transfer medium or a mixture thereof to destroy tumors, to stimulate the immune system, for magnetic drug targeting, for cell fusion, for gene transfer, as a contrast medium, as a magnetic ion exchanger and as magnetic adsorbents for separation processes.

5. Superparamagnetic particles, consisting of particles selected from the group consisting of
   (a) small superparamagnetic one-domain particles selected from the group consisting of iron hydroxide, iron oxide hydrate, iron oxide, mixed iron oxide, and iron with a particle size ranging between 3 and 50 nanometers; and (b) dispersion stable, physiological degradable aggregates with a particle size ranging between 10 and 1000 nanometers, whereby the aggregate comprises several small superparamagnetic one-domain particles selected from the group consisting of iron hydroxide, iron oxide hydrate, iron oxide, mixed iron oxide or iron with a particle size ranging between 3 and 50 nanometers; and the mixtures of (a) and (b);

wherein to the surfaces of the particles or aggregates or mixtures thereof are bound on binding sites on said surfaces, (c) substances selected from the group consisting of
  (i) mono or polyhydroxylic group-containing or both groups containing aromatic substances, selected from the group consisting of benzenoids, coumarins, lignans, terphenyls, flavonoids, tannins, xanthenes, benzophenones, naphthalenes, naphthoquinones, anthraquinones, anthracyclines, polycyclic condensated aromatic compounds and their phosphate, diphosphate, polyphosphate, thiophosphate, phosphonate, thiophosphonate, carboxylate, sulphate, mercapto or silantriol group-containing derivatives; and in addition to the substances (c) and on their binding sites are chemically bound organic substances (d), selected from the group consisting of (vi) phosphate, diphosphate, carboxylate, polyphosphate, thiophosphate, phosphonate, thiophosphonate, sulphate, sulphonate, mercapto, carboxylate silantriol, trialkoxy silane group-containing polyalkylene glycols and carbohydrates; and
  (vii) phosphate group-containing nucleotides, the oligomers thereof or the polymers thereof; and
  (viii) the alkyl, aryl, alkyl-aryl-polyethylene glycol phosphates or -phosphonates, phosphates or phosphonates of the substance copolymerides from polyethylene glycol (PEG) and polypropylene glycol (PPG), selected from among the substance copolymerides $(PEG)_n\text{-}(PEG)_m$, $(PEG)_n\text{-}(PPG)_m\text{-}(PEG)_n$, $(PPG)_m\text{-}(PEG)_n\text{-}(PPG)_m$; and whereby n and m are positive whole numbers, selected for PEG in the range of 4 to 1000, for PPG in the range of 3 to 12 and for PEG-PPG substance copolymerides in the range of 3 to 140;

(ix) nitrogenous polysaccharides, selected from among mucopolysaccharides, glycoproteids, chitins, as well as their derivatives and denaturation products; and mixtures of substances of the groups (vi)–(ix).

* * * * *